United States Patent
Ullrich et al.

(10) Patent No.: US 8,217,769 B2
(45) Date of Patent: *Jul. 10, 2012

(54) ACTUATING A TACTILE SENSATION IN RESPONSE TO A SENSED EVENT

(75) Inventors: Christopher J. Ullrich, Ventura, CA (US); Michael D. Graham, San Jose, CA (US); Jason D. Fleming, San Jose, CA (US)

(73) Assignee: Immersion Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/022,086

(22) Filed: Feb. 7, 2011

(65) Prior Publication Data

US 2011/0128133 A1      Jun. 2, 2011

Related U.S. Application Data

(63) Continuation of application No. 12/019,213, filed on Jan. 24, 2008, now Pat. No. 7,898,396.

(51) Int. Cl.
*H04B 3/36* (2006.01)

(52) U.S. Cl. .................. 340/407.1; 340/600; 340/573.1

(58) Field of Classification Search ............... 340/407.1, 340/539.27–539.29, 7.6, 600, 573.1, 825.19
See application file for complete search history.

(56) References Cited

U.S. PATENT DOCUMENTS

| | | | |
|---|---|---|---|
| 4,414,984 A * | 11/1983 | Zarudiansky | 600/587 |
| 4,968,567 A | 11/1990 | Schisselbauer | |
| 5,727,550 A | 3/1998 | Montecalvo | |
| 6,774,806 B1 * | 8/2004 | Bannell et al. | 340/679 |
| 2002/0065453 A1 | 5/2002 | Lesho et al. | |
| 2002/0107436 A1 | 8/2002 | Barton et al. | |
| 2003/0214408 A1 | 11/2003 | Grajales et al. | |
| 2004/0010390 A1 | 1/2004 | Kelly, Jr. et al. | |
| 2004/0039254 A1 | 2/2004 | Stivoric et al. | |
| 2005/0142093 A1 | 6/2005 | Skover et al. | |
| 2006/0161218 A1 | 7/2006 | Danilov | |
| 2007/0003115 A1 | 1/2007 | Patton et al. | |
| 2007/0100666 A1 | 5/2007 | Stivoric et al. | |
| 2008/0084298 A1 | 4/2008 | King | |

OTHER PUBLICATIONS

International Search Report and Written Opinion, PCT/2008/087108.

(Continued)

*Primary Examiner* — Jennifer Mehmood
*Assistant Examiner* — Hongmin Fan
(74) *Attorney, Agent, or Firm* — Squire Sanders (US) LLP

(57) ABSTRACT

Systems and methods for actuating a tactile stimulation in response to detecting a specific event associated with exposure to a particular environmental or physiological condition are described herein. A tactile stimulation device, according to one of several implementations, comprises a sensing layer, an actuating layer, and an adhesive layer. The sensing layer, which is sensitive to exposure to a particular condition, is configured to sense when a specific event associated with exposure to the particular condition occurs. The actuating layer is configured to provide a tactile stimulation to a human subject when the specific event occurs. The adhesive layer is configured to affix the sensing layer and actuating layer with respect to a surface portion of the skin of the human subject such that the human subject can sense the tactile stimulation provided by the actuating layer. The sensing layer, actuating layer, and adhesive layer can be bonded together to form a relatively flat structure.

20 Claims, 3 Drawing Sheets

OTHER PUBLICATIONS

Official Communication issued in PCT/2008/087108, mailed Aug. 5, 2010.

Official Communication issued in the corresponding PCT Application No. PCT/US2008/087108, mailed Aug. 5, 2010.

* cited by examiner

ACTUATING A TACTILE SENSATION IN RESPONSE TO A SENSED EVENT

CROSS-REFERENCE TO RELATED APPLICATIONS

This application is a continuation of U.S. patent application Ser. No. 12/019,213, filed on Jan. 24, 2008, the specification of which is hereby incorporated by reference.

TECHNICAL FIELD

The present disclosure generally relates to devices for sensing environmental or physiological conditions. More particularly the present disclosure relates to providing a tactile sensation in response to sensing an event associated with such a condition.

BACKGROUND

Sunbathers wanting to achieve a good tan without burning are often unaware of the proper amount of ultraviolet (UV) radiation that they are actually receiving from the sun. Because of various factors regarding the direction and angle of the rays of the sun with respect to the skin of a sunbather, the amount of actual UV radiation can dynamically change over time. Also, reflections of the sun's rays off of sand, water, snow, etc. can increase the effect of the UV rays. Attempting to gauge the level of UV exposure can therefore be an unpredictable process with undesirable results.

In many cases, a sunbather may attempt to judge the amount of UV exposure by estimating or measuring a certain amount of time. However, because the level of UV exposure does not necessarily correlate to time, this technique is not always accurate. Another technique for monitoring UV exposure is by using a special meter that measures radiation levels. With this device, a sunbather can enter a certain desired amount of exposure and the device will provide an indication signal when that exposure level has been reached.

However, at least one disadvantage of these types of UV exposure meters is that they must be carried around wherever the sunbather goes. Also, without adequately charged batteries, the device may not be powered sufficiently for proper operation. Also, the device must be set up in a place that has similar radiation exposure as that of the sunbather. It would therefore be desirable to overcome these and other shortcomings of the conventional systems and methods.

SUMMARY

Tactile stimulation devices are described in the present disclosure for providing a tactile stimulation in response to the occurrence of a specific event associated with a sensed condition. In one of several possible embodiments, a tactile stimulation device comprises a sensing layer that is sensitive to exposure to a particular condition. The sensing layer is configured to sense when a specific event associated with exposure to the particular condition occurs. The tactile stimulation device also includes an actuating layer configured to provide a tactile stimulation to a human subject when the specific event occurs. Furthermore, the tactile stimulation device comprises an adhesive layer configured to affix the sensing layer and actuating layer with respect to a surface portion of the skin of the human subject such that the human subject can sense the tactile stimulation provided by the actuating layer. In some embodiments, the sensing layer, actuating layer, and adhesive layer are bonded together to form a relatively flat structure.

Other features, advantages, and implementations of the present disclosure, not expressly disclosed herein, will be apparent to one of ordinary skill in the art upon examination of the following detailed description and accompanying drawings. It is intended that such implied implementations of the present disclosure be included herein.

BRIEF DESCRIPTION OF THE DRAWINGS

The components in the following figures are not necessarily drawn to scale. Instead, emphasis is placed upon clearly illustrating the general principles of the present disclosure. Reference characters designating corresponding components are repeated as necessary throughout the figures for the sake of consistency and clarity.

DETAILED DESCRIPTION

Tactile stimulation devices and methods of manufacturing these tactile stimulation devices are described herein. The tactile stimulation devices of the present disclosure are designed to sense an exposure to an environmental condition, e.g. ultraviolet (UV) radiation, or a physiological condition, e.g. heart rate. At the occurrence of a specific event associated with the sensed environmental or physiological condition, a tactile stimulation is provided to a subject, e.g. human, to indicate that the specific event has occurred.

The elements of the tactile stimulation devices described herein can be integrated into a relatively small unit. In some embodiments, the elements may include relatively thin layers bonded together to form a substantially planar unit. Furthermore, the tactile stimulation devices may be formed on flexible layer to allow the devices to conform to the surface on which they are placed.

The tactile stimulation devices are capable of providing enough power to operate for a limited amount of time, depending on the particular application. In some cases, the amount of stored energy is sufficient for a one-time use, but in other cases, the devices can be used repeatedly. Since the devices are self-powered, the user does not have to worry about adding batteries or other power sources. Furthermore, the devices can be manufactured relatively inexpensively and can therefore be disposed of after use.

In some embodiments, the tactile stimulation devices may include an adhesive that is capable of holding the device adjacent to or on a person's skin. In this respect, the device may have an appearance that is similar to a person's skin such as some forms of an adhesive bandages. Since it can be affixed to the skin, the device can be used to accurately sense certain physiological conditions or even environmental conditions that are also experienced by the user. In contrast to the conventional systems that use a bulky UV meter that may require relocation, the tactile stimulation devices of the present disclosure are present with the user as long as they stay attached and therefore there is less need for the user to worry about location since it experiences substantially the same exposure as the skin surrounding the attached device.

Although many examples described in the present disclosure relate to monitoring a level of UV radiation for people concerned about sun exposure, it should be understood that the teachings of the present disclosure may also encompass applications where other environmental or physiological conditions are monitored. Such other applications will become apparent to one of ordinary skill in the art from an understanding of the present disclosure.

Figure 1:
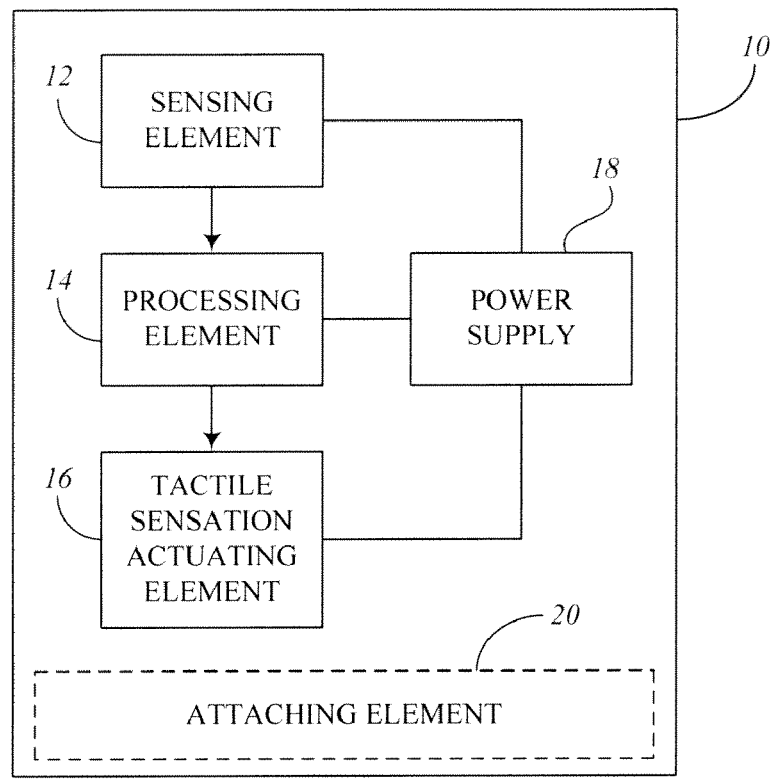
FIG. 1 is a block diagram illustrating an embodiment of a tactile stimulation device.

FIG. 1 is a block diagram of a tactile stimulation device 10 according to one embodiment. In this embodiment, tactile stimulation device 10 includes a sensing element 12, a processing element 14, a tactile sensation actuating element 16, a power supply 18, and an attaching element 20. In some implementations, sensing element 12, processing element 14, and tactile sensation actuating element 16 may be integrated in any desirable combination. For example, some implementations may include a single element including the functionality of sensing element 12 and processing element 14. Furthermore, power supply 18 may be integrated with processing element 14 or another element.

Sensing element 12 includes any suitable materials, components, circuitry, reactive elements, etc., which are sensitive to or are capable of sensing one or more environmental or physiological conditions. Sensing element 12 can also be in the form of a specialized paint that is sensitive to certain conditions. In this regard, the material may alternatively be configured to change from opaque to transparent, or vice versa. The transparency change may in some cases be an irreversible change. In some embodiments, sensing element 12 includes a disintegrating or decomposing material that disintegrates in response to exposure to a particular condition. In some instances, sensing element 12 includes a radio frequency (RF) receiver for sensing RF signals. In each instance, however, sensing element 12 is designed to specifically sense an exposure to a particular condition.

When exposed to the particular condition, sensing element 12 may further monitor the occurrence of a specific event associated with the exposure to the particular condition. For example, in the case of monitoring UV radiation, sensing element 12 may be configured to be sensitive to UV radiation, and a specific event related to monitoring UV radiation may be defined by a particular point in time when the amount of UV radiation reaches a predetermined threshold. When the specific event is detected by sensing element 12, a signal is provided to processing element 14 for further processing.

Sensing element 12 may be configured in any suitable manner to sense one or more of any number of possible environmental or physiological conditions, depending on the application. Non-limiting examples of possible environmental conditions sensed by sensing element 12 include sensing radiation, such as UV radiation (UVA rays, UVB rays, etc.), radiation within the visible light spectrum, x-ray radiation, etc. With respect to applications involving the sensing of radiation, sensing element 12 may be configured to sense when a specific level of radiation has been reached. In this case, the specific event as mentioned above relates to a specific accumulated level of radiation exposure over a length of time. In other implementations, the specific event may simply be defined by any initial exposure to particular types of radiation being monitored. Other non-limiting examples of conditions that can be sensed by sensing element 12 include the sensing of oxygen, moisture, humidity, ambient temperature, etc.

Examples of sensing physiological conditions include sensing body temperature, heart rate, blood sugar, perspiration, etc. In these examples, the specific event to be determined may be the detection of a level or value that is outside a normal or acceptable range or the detection of the condition reaching a predetermined threshold.

In one embodiment in which body temperature is sensed, sensing element 12 can be configured to track a woman's skin temperature over a period of time. By monitoring a woman's basal body temperature (BBT), an estimation of the time of ovulation can be made. Because of the pattern of temperature changes before, during, and after ovulation, tactile sensation actuating element 16 can be configured to indicate when the woman is likely the most fertile. Normally, a woman's BBT is lower (97°-97.5° F.) prior to ovulation and increases by about one-half of a degree to one degree during ovulation. After ovulation, menstruation begins and BBT falls. Sensing element 12 or processing element 14 can be designed to monitor BBT to determine an increased likelihood of conception. Tactile sensation actuating element 16 can be configured to provide a haptic sensation at the beginning of ovulation, at the end of ovulation, or both.

Sensing element 12 sends a signal to processing element 14 when the specific event occurs. In other embodiments, sensing element 12 may continually provide values of a sensed parameter to processing element 14, which, in this case, determines when the specific event occurs. Sensing element 12 and processing element 14 communicate with each other using any suitable transmission lines or wireless communication components. When processing element 14 receives an indication of the occurrence of the specific event or determines the occurrence of the specific event itself, processing element 14 sends a command to tactile sensation actuating element 16 to provide a tactile stimulation to the intended subject.

Processing element 14 may include any suitable combination of digital and/or analog components. In some embodiments, processing element 14 may be printed on a thin layer, such as a tape. The printing process to form element 14 may include lithographic or other suitable form of printing. Processing element 14 in some cases may be embedded or integrated with sensing element 12 and/or tactile sensation actuating element 16.

In response to the command to provide a tactile stimulation, tactile sensation actuating element 16 provides the subject with a stimulation that is strong enough to be felt or sensed by the subject. The stimulation may have a short duration depending on the type of stimulation provided and the amount of charge stored in power supply 18. One example of a type of stimulation provided by the tactile sensation actuating element 16 is an electrical stimulation. For example, the electrical stimulation may be a high voltage pulse, an electrostatic discharge, an electrical current, or other suitable type of electrically generated sensation. In other implementations, the tactile stimulation may be a chemical stimulation, such as the application of a chemical compound that causes a temporarily yet noticeable discomfort or irritation of the skin.

Tactile sensation actuating element 16 may provide other types of tactile stimulation to the subject. For example, tactile sensation actuating element 16 may include a piezoelectric component that vibrates in response to a voltage. In still another example, tactile sensation actuating element 16 may contain a deformable material that expands or contracts in response to an electrical or chemical stimulus. In this case, the deformable material, when attached to the skin of a human, can provide a stretching or compressing sensation to the human when it shrinks or expands. Other suitable types of tactile stimulations can be provided by tactile sensation actuating element 16 as desired.

In one embodiment, power supply 18 is a self-sufficient device that does not rely on external power sources. Power supply 18 supplies power to sensing element 12, processing element 14, and/or tactile sensation actuating element 16 as needed. Particularly, power supply 18 provides a high electrical pulse to tactile sensation actuating element 16 to allow this element to apply a pulse-type stimulation to the subject. Power supply 18 may include any suitable type of power generating components. For example, power supply 18 may rely on a chemical reaction, similar to the chemical reaction within a battery, for providing power. Another example of the configuration of power supply 18 includes the generation of power by a radioactive reaction. In addition, other implementations of power supply 18 may include the use of a barrier material separating two inert chemical or radioactive components that can chemically or radioactively react when combined. To initiate the reaction in this case, the barrier material can be disintegrated using some type of stimulus, thereby breaking the barrier between the reacting components.

The distribution of power provided by power supply 18 may include specific initiation factors for determining when to provide power to other elements of tactile stimulation device 10. Power supply 18 might begin providing power when sensing element 12 is to begin sensing exposure to the particular condition. On the other hand, power supply 18 may begin providing power when the specific event associated with the particular condition is detected. In other embodiments, power supply 18 may supply a first amount of power when sensing element 12 is to begin sensing and supply a second amount of power when the specific event occurs.

Some implementations of power supply 18 include storing power or an electrical charge from the environment. For example, power supply 18 may include solar cells for absorbing energy from the sun. In other embodiments, power supply 18 may inductively store charge from external RF signals or electromagnetic fields. In one embodiment, power supply 18 can store about 10 minutes of charge in an internal capacitor. In still other implementations, power supply 18 may include a micro-electromechanical system (MEMS). As a MEMS device, power supply 18 can leverage user motion to capture and store energy and may contain, for example, micro-springs or other suitable devices for providing physical forces on a small scale.

Tactile stimulation device 10 of FIG. 1 further includes attaching element 20. However, an attaching element may be omitted in embodiments in which tactile stimulation device 10 can be held in the hand of a subject or placed in a pocket of a subject's clothing. In these cases, a tactile stimulation provided by tactile sensation actuating element 16 can still be felt by the subject without attachment to the subject's skin or clothing.

Generally, attaching element 20 is configured to affix or hold the elements of tactile stimulation device 10 close to, adjacent to, or in contact with the subject, e.g., a surface portion of the skin of a human subject. By attaching on the skin or holding against the skin, for example, the subject can more easily feel a tactile stimulation. In some embodiments, it may be necessary to use attaching element 20 to attach the tactile stimulation device 10 directly to the skin, such as in the case of a chemical-type stimulation. In some situations, tactile stimulation device 10 can be attached or held against a portion of skin underneath a garment. This situation may be acceptable when the garment does not adversely affect the sensitivity of sensing element 12 to the particular condition being monitored. The scope of the present disclosure may further include a garment specially designed with a hole or cut-out section through which tactile stimulation device 10 can be attached to the skin and exposed to the particular environmental condition.

In some embodiments, attaching element 20 includes an adhesive material for attaching to a subject or to a garment worn by the subject. In other embodiments, attaching element 20 may include a band of material having a fastening mechanism. In this case, the band may be wrapped around a finger, wrist, arm, ankle, leg, etc., and the fastening mechanism may include an adhesive material, clip, Velcro™, etc. Instead of including a fastening mechanism, as an alternative, the band of material may simply be tied around a portion of the body of the subject. In some embodiments, attaching element 20 may include fastening means for fastening the elements of tactile stimulation device 10 to a garment using a clip, pin, etc. The fastening means may be of a type designed for long term attachment, such as by the use of stitches sewn between tactile stimulation device 10 and a garment.

Specialized applications of tactile stimulation device 10, in addition to corresponding structure, is further described here. As suggested above, sensing element 12 can sense electromagnetic radiation within any desirable frequency spectrum. Regarding UV radiation, tactile stimulation device 10 can indicate when sensing element 12 is exposed to a certain level of UV radiation. The sensitivity of sensing element 12 from one tactile stimulation device 10 to another can be set at different levels depending on the particular application. In this way, one tactile stimulation device can provide an indication of a first level of tanning while another tactile stimulation device can provide an indication of a second level of tanning. Tactile stimulation device 10 can also be used to sense certain exposure levels of other types of radiation, such as visible light radiation, x-ray radiation, etc.

Sensing element 12 may include an RF identification (RFID) tag and may be configured to detect RF signals. Applications in this respect may include, for example, a queue indication system, proximity sensor system, wireless feedback for gaming modules, etc. The queue indication system, as mentioned herein, may refer to a tactile indication when someone's turn in line has come up. In this way, only the person wearing the respective tactile stimulation device receives the private tactile stimulation to indicate that it is his or her turn to receive service, i.e. at a restaurant or store.

The proximity sensor system, as mentioned herein, may refer to a system where a central RF transmitter provides a constant signal. When the strength of the received signal by sensing element 12 decreases below a predetermined threshold, a tactile stimulation can be provided to indicate that the user is too far from the central transmitter. This implementation can be used in a manner similar to an "invisible" fence for training pets or small children to stay within certain parameters. The proximity sensor system can also be used in a manner to detect when RF receiver of sensing element 12 receives RF signal having a strength that exceeds normal levels. In this case, the system could be used to provide a tactile stimulation if someone gets too close to a central transmitter, which may be located near items that are meant not to be disturbed.

Another application of tactile stimulation device 10 can be for providing a private "alarm clock", timer, metronome, or other clocking device for an individual wearing the device. In this application, the sensing element 12 may simply detect the occurrence of an initiating event. For example, removing a protective layer from tactile stimulation device 10 may cause a reaction that defines the initiating event. The initiating event may also include the first detection of an environmental condition, such as radiation of some type. The initiating event can then be used to start a clock or timer, which may be part of processing element 14, for example. The clock or timer may be configured to count down for a certain period of time, e.g. five minutes, ten minutes, 30 minutes, etc. The specific event in this case occurs after the elapsed time and a tactile stimulation can be provided to indicate the elapse of the certain time period. Other applications involving a clock or timer may include providing tactile stimulation of a steady beat or rhythm for use by a musician or for pacing a runner's gait.

Other applications of tactile stimulation device 10 include measuring one or more conditions of a human, such as body temperature, heart rate, heart rhythms, blood sugar, or other conditions or vitals of the human body. In this case, any of these or other particular conditions can be sensed by sensing element 12. If the level or value of the condition falls outside of a normal or acceptable range, the tactile sensation actuating element 16 can provide a warning to the user that the condition is abnormal. Since such an application may be essential for the health of the person, a strong tactile stimulation may be provided in this case that would not be easily missed.

Figure 2:
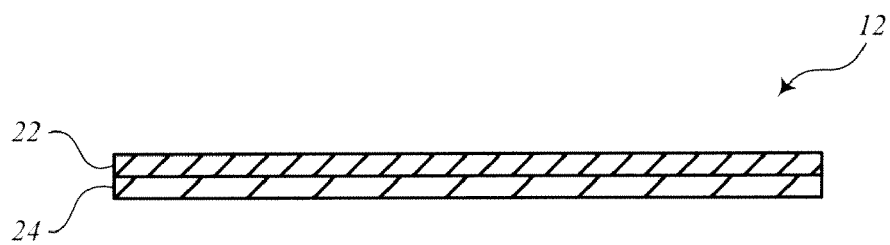
FIG. 2 illustrates a cross-sectional side view of a first embodiment of the sensing element shown in FIG. 1.

FIG. 2 is a cross-sectional side view of sensing element 12 shown in FIG. 1 according to one embodiment. In this embodiment, sensing element 12 includes a first layer 22 and a second layer 24. First layer 22 is designed with a particular thickness and sensitivity to gradually disintegrate or decompose when exposed to a particular condition. After being exposed to the particular condition for a length of time, first layer 22 is designed to completely disintegrate or to disintegrate to such a degree that second layer 24 is exposed. When the degree of disintegration of first layer 22 reaches a particular threshold, second layer 24 is exposed and senses that the exposure to the particular condition has reached the threshold. Notification can then be provided to processing element 14 for processing or for instructing tactile sensation actuating element 16 to provide a tactile stimulation.

Regarding the embodiments involving exposure to radiation, when first layer 22 disintegrates after a certain amount of exposure to the radiation, the subject, e.g. human, receives the tactile stimulation that is meant to alert the human that exposure has reached a particular level. For a sunbather, for example, this may mean that it is time to stop sunbathing. The thickness or sensitivity of first layer 22 can define the amount of UV exposure before the tactile stimulation is provided. In this respect, first layer 22 of different tactile stimulation devices can be grouped depending on thickness or sensitivity. Thus, a sunbather can have a choice of different levels of UV exposure. Someone desiring a darker tan may use a device having a thicker or less sensitive first layer 22, while someone desiring a lighter tan may use a device having a thinner or more sensitive first layer 22.

Figure 3:
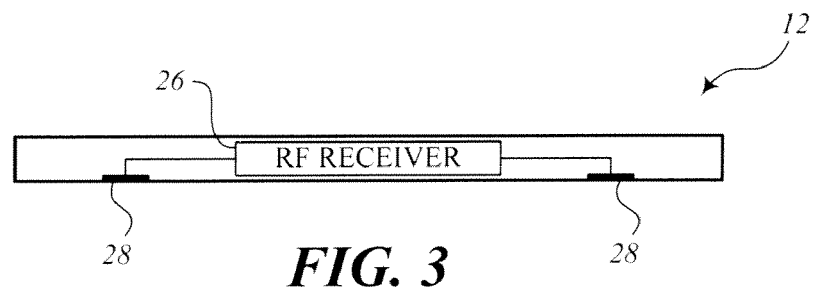
FIG. 3 illustrates a cross-sectional side view of a second embodiment of the sensing element shown in FIG. 1.

FIG. 3 is a cross-sectional side view of sensing element 12 shown in FIG. 1 according to one embodiment. In this embodiment, sensing element 12 includes an RF receiver 26 and communication ports 28. RF receiver 26 is tuned to receive RF signals from an external transmitter that can be used in conjunction with the tactile stimulation devices described herein. In this case, RF receiver 26 is sensitive to RF signals within a particular frequency band. RF receiver 26 may also be designed to detect a value carried in the RF signal that identifies the respective device. For example, in the embodiment where the tactile stimulation device is used in a queue indication system, such as for waiting a turn at a restaurant or store, RF receiver 26 may be sensitive to only those values that pertain to that device. Otherwise, values for other devices would indicate other people's turns.

FIGS. 4-7 illustrate embodiments of tactile stimulation devices that are configured to sense a particular condition and determine when a specific event occurs with respect to exposure to the particular condition. In response to determining the specific event, the tactile stimulation devices actuate a tactile sensation for a subject, e.g. human. The element described in the embodiments of FIGS. 4-7 may be related to elements with respect to tactile stimulation device 10 of FIG. 1 and may include similar respective functions. However, in these embodiments, the elements of the tactile stimulations devices are formed as relatively thin layers. When bonded together, the elements can form a multi-layered tape that can be either flexible or rigid. For the sake of illustrating certain aspects, FIGS. 4-7 do not necessarily include all elements that may be present. It should be understood that certain portions, elements, aspects of each embodiment of FIGS. 4-7 may also be included in other embodiments as well.

These tactile stimulation devices can be one-use, disposable-type devices or, in the alternative, can be reusable. Because they can be configured on a small scale, the tactile stimulation can provide a private indication for the wearer only. When embodied as a tape, the devices can be provided on a roll or sheet and can be separated as needed. In addition, the tactile stimulation devices can include any shape, design, colors, patterns, etc., and may have figures thereon, similar to images of a tattoo.

Figure 4:
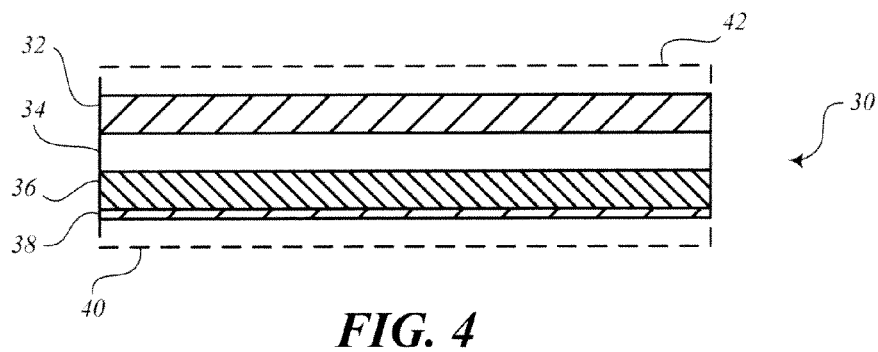
FIG. 4 illustrates a cross-sectional side view of an embodiment of a tactile stimulation device.

FIG. 4 is a cross-sectional side view of a tactile stimulation device 30 according to one embodiment. In this embodiment, tactile stimulation device 30 includes a sensing layer 32, processing layer 34, actuating layer 36, and adhesive layer 38. In some embodiments, tactile stimulation device 30 may also include a removable layer 40 that protects adhesive layer 38 until the user is ready to use tactile stimulation device 30. Also, tactile stimulation device 30 may also include another removable layer 42 that protects sensing layer 32 until ready for use. Removable layer 42 may be designed to specifically prevent exposure of the particular condition to which sensing layer 32 is sensitive. In some embodiments, removable layer 42 may trigger an initiating event when removed, thereby indicating a start of the sensed condition or the start of a certain time period.

Figure 5:
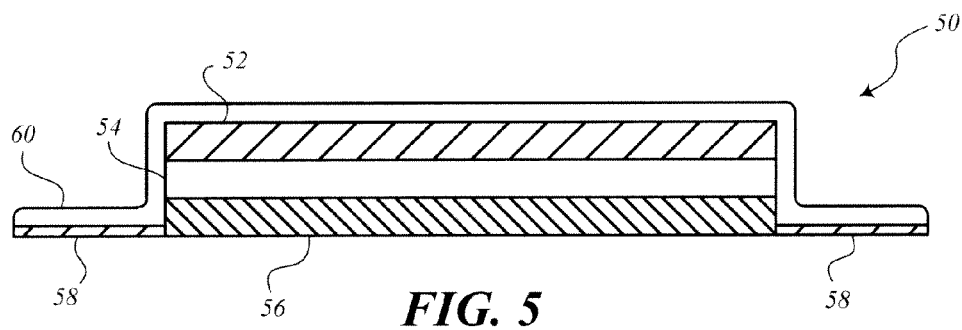
FIG. 5 illustrates a cross-sectional side view of another embodiment of a tactile stimulation device.

FIG. 5 is a cross-sectional side view of a tactile stimulation device 50 according to one embodiment. In this embodiment, tactile stimulation device 50 includes a sensing layer 52, processing layer 54, actuating layer 56, and one or more adhesive layers 58. Tactile stimulation device 50 also includes a laminate layer 60 that protects the layers from undesired environmental conditions. In this embodiment, adhesive layers 58 may be positioned to the side of actuating layer 56 in order that actuating layer 56 can be in direct contact with the skin. Other configurations can be used for positioning actuating layer 56 near or in contact with the skin.

Figure 6A:
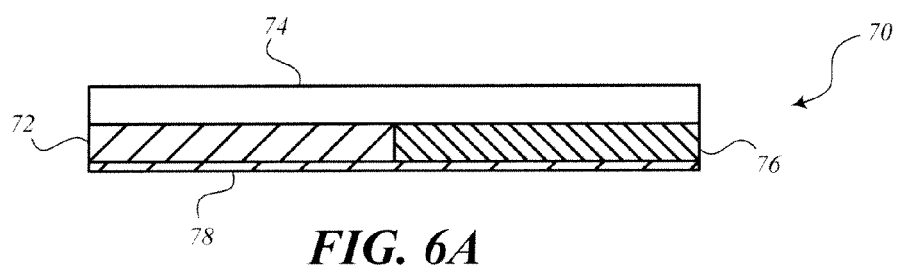
FIGS. 6A and 6B illustrate cross-sectional side views of other embodiments of tactile stimulation devices.

FIG. 6A is a cross-sectional side view of a tactile stimulation device 70 according to one embodiment. In this embodiment, tactile stimulation device 70 includes a sensing layer 72, processing layer 74, actuating layer 76, and adhesive layer 78. Tactile stimulation device 70 in this case includes sensing layer 72 and actuating layer 76 in the same layer or next to each other at the same height. This configuration may be beneficial to allow sensing layer 72 to be closer to the skin when the sensed condition corresponds to a physiological condition. In this arrangement, sensing layer 72 might be able to more easily detect the particular physiologic condition. Also, the configuration of this embodiment places actuating layer 76 close to or against the skin such that a tactile stimulation can be more easily felt by the person.

Figure 6B:
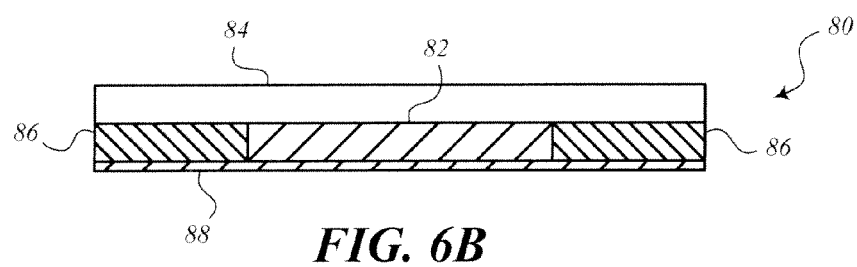

FIG. 6B is similar to FIG. 6A and illustrates a cross-sectional side view of a tactile stimulation device 80 according to another embodiment. In this embodiment tactile stimulation device 80 includes a sensing layer 82, processing layer 84, one or more actuating layers 86, and adhesive layer 88. Again, sensing layer 82 and actuating layers 86 are positioned closest to the skin for greater communication with the physiological conditions and nerve endings of the skin. In this arrangement, however, sensing layer 82 is centralized to allow a more precise positioning of the device on a particular portion of the body for detecting a certain physiological condition.

Figure 7A:
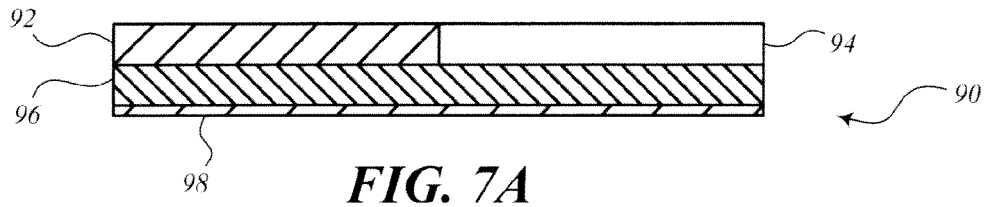
FIGS. 7A and 7B illustrate cross-sectional side views of yet other embodiments of tactile stimulation devices.

FIG. 7A is a cross-sectional side view of a tactile stimulation device 90 according to one embodiment. In this embodiment, tactile stimulation device 90 includes a sensing layer 92, processing layer 94, actuating layer 96, and adhesive layer 98. Tactile stimulation device 90 includes sensing layer 92 and processing layer 94 next to each other at the same height.

Figure 7B:
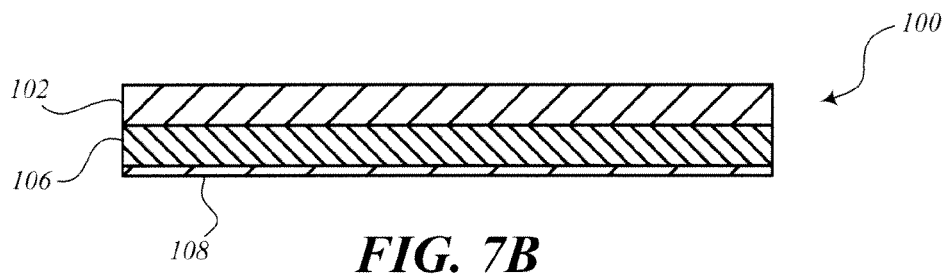

FIG. 7B illustrates a cross-sectional side view of a tactile stimulation device 100 according to another embodiment. In this embodiment, tactile stimulation device 100 includes a sensing/processing layer 102, actuating layer 106, and adhesive layer 108. Sensing/processing layer 102 may have the same functions as each of the sensing layers and processing layers as described above. This arrangement may be used when the sensing and processing functions are integrated together or can be combined together. These and other arrangements may be used for miniaturizing the tactile stimulation devices while providing the functions described herein.

Figure 8:
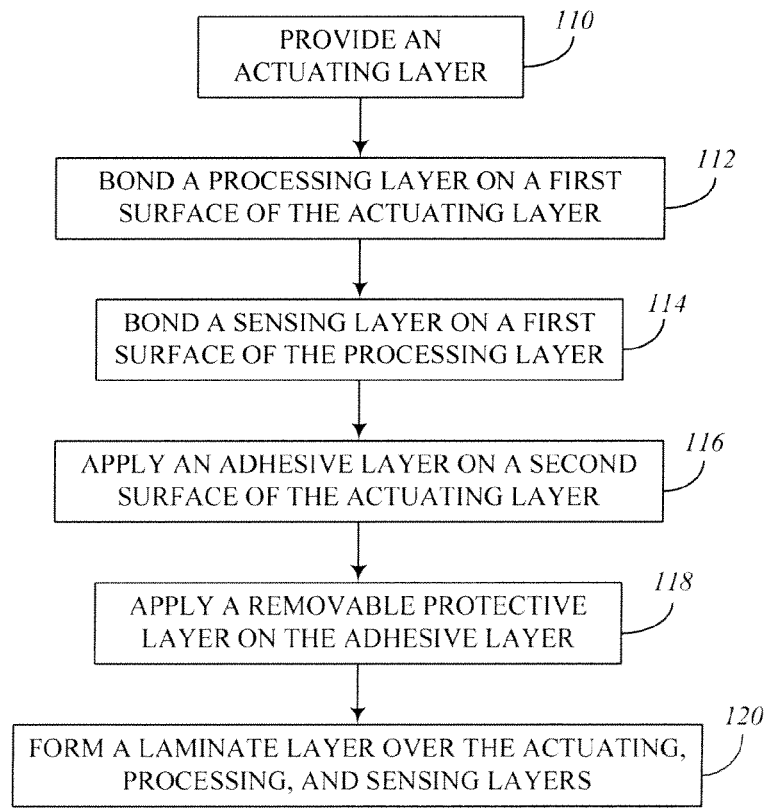
FIG. 8 is a flow chart illustrating an embodiment of a method of manufacturing one or more of the tactile stimulation devices of FIGS. 4-7.

FIG. 8 is a flow chart illustrating a method of manufacturing a tactile stimulation device according to one embodiment. As indicated in block 110, an actuating layer is provided. In block 112, a processing layer is bonded on a first surface of the actuating layer. In block 114, a sensing layer is bonded on a first surface of the processing layer. Generally, these blocks describe the forming of a multi-layered device for sensing a specific event associated with an exposure to a particular environmental or physiological condition. As suggested above, other methods of manufacturing a tactile stimulation device having these three elements or layers can be realized from an understanding of the description of FIGS. 4-7. Blocks 116-120 in some embodiments may be omitted from the manufacturing process if desired.

In block 116, an adhesive layer is applied to a second surface of the actuating layer. In block 118, a removable protective layer is applied to the adhesive layer. In some embodiments, a second removable protective layer may be applied to the sensing layer for protecting the sensing layer before use. In block 120, a laminate is formed over the actuating, processing, and sensing layers. It should be understood that one or more of the steps, processes, and/or operations described herein may be executed substantially simultaneously or in a different order than explicitly described, as would be understood by one of ordinary skill in the art.

The embodiments described herein merely represent examples of implementations and are not intended to necessarily limit the present disclosure to any specific embodiments. Instead, various modifications can be made to these embodiments as would be understood by one of ordinary skill in the art. Any such modifications are intended to be included within the spirit and scope of the present disclosure and protected by the following claims.

We claim:

1. A tactile stimulation device comprising:
a sensing element that is sensitive to exposure to a particular condition;
a tactile sensation actuating element configured to provide a tactile stimulation to a subject when a specific event associated with exposure to the particular condition occurs;
an attaching element configured to affix the sensing element and the tactile sensation actuating element with respect to the subject such that the subject can sense the tactile stimulation provided by the tactile sensation actuating element; and
a flexible element that conforms to a surface, wherein the sensing element, the tactile sensation actuation element, and the attaching element are formed on the flexible element.

2. The tactile stimulation device of claim 1, further comprising a power supply that supplies power to the sensing element and the tactile sensation actuating element, wherein the power is sufficient so that the tactile stimulation device is used repeatedly.

3. The tactile stimulation device of claim 1, wherein the sensing element comprises a paint that is sensitive to a particular condition.

4. The tactile stimulation device of claim 1, wherein the tactile sensation actuating element is further configured to provide the tactile stimulation of a steady beat to the subject.

5. The tactile stimulation device of claim 1, wherein the sensing element comprises a first layer and a second layer, the first layer being configured to disintegrate when exposed to the particular condition.

6. The tactile stimulation device of claim 1, wherein the first element is configured to determine when the specific event occurs.

7. The tactile stimulation device of claim 1, wherein the tactile stimulation provided to the subject comprises one of an electrical stimulation, a chemical stimulation, a piezoelectric stimulation, or a compressing or expanding force provided by a deforming material.

8. The tactile stimulation device of claim 1, wherein the attaching element comprises at least one of an adhesive or a band having a fastening mechanism.

9. The tactile stimulation device of claim 8, wherein the attaching element comprises means for fastening to a garment worn by the subject.

10. The tactile stimulation device of claim 1, wherein the specific event is the complete disintegration of the first layer.

11. A method for manufacturing tactile stimulation tape, the method comprising:
providing a flexible layer that conforms to a surface;
bonding an actuating layer to the flexible layer, wherein the actuating layer is configured to create a tactile stimulation for a human subject;
bonding a processing layer on the actuating layer; and
bonding a sensing layer on the processing layer;
wherein the sensing layer is configured to sense the occurrence of a specific event associated with an exposure of the sensing layer to a particular condition.

12. The method of claim 11, further comprising providing a power supply that supplies power to the sensing element and the actuating layer, wherein the power is sufficient so that the tactile stimulation tape is used repeatedly.

13. The method of claim 11, wherein the sensing layer comprises a paint that is sensitive to a particular condition.

14. The method of claim 11, wherein the actuating layer is further configured to create the tactile stimulation of a steady beat for the subject.

15. The method claim 11, further comprising applying an adhesive layer on the actuating layer, the adhesive layer adapted to affix the tactile stimulation tape with respect to a surface portion of the skin of the human subject such that the human subject can sense a tactile stimulation created by the actuating layer.

16. A tactile stimulation device comprising:

a sensing element that is sensitive to exposure to a particular condition;

a tactile sensation actuating element configured to provide a tactile stimulation to a subject when a specific event associated with exposure to the particular condition occurs;

an attaching element configured to affix the sensing element and the tactile sensation actuating element with respect to the subject such that the subject can sense the tactile stimulation provided by the tactile sensation actuating element; and a power supply that supplies power to the sensing element and the tactile sensation actuating element, wherein the power is sufficient so that the tactile stimulation device is used repeatedly.

17. The tactile stimulation device of claim 16, wherein the sensing element comprises a paint that is sensitive to a particular condition.

18. The tactile stimulation device of claim 17, further comprising a flexible element that conforms to a surface.

19. The tactile stimulation device of claim 16, wherein the tactile sensation actuating element is further configured to provide the tactile stimulation of a steady beat to the subject.

20. The tactile stimulation device of claim 16, wherein the sensing element comprises a first layer and a second layer, the first layer being configured to disintegrate when exposed to the particular condition.

\* \* \* \* \*